US005482853A

United States Patent [19]
Sandmeyer

[11] Patent Number: 5,482,853
[45] Date of Patent: * Jan. 9, 1996

[54] POSITION-SPECIFIC INSERTION VECTORS AND METHOD OF USING SAME

[75] Inventor: Suzanne B. Sandmeyer, Corona del Mar, Calif.

[73] Assignee: The Regents of the University of California, Oakland, Calif.

[*] Notice: The portion of the term of this patent subsequent to Mar. 8, 2011, has been disclaimed.

[21] Appl. No.: 128,483

[22] Filed: Sep. 28, 1993

Related U.S. Application Data

[63] Continuation of Ser. No. 895,333, Jun. 8, 1992, Pat. No. 5,292,662, which is a continuation of Ser. No. 276,201, Nov. 23, 1988, abandoned.

[51] Int. Cl.$^6$ .......................... C12N 15/63; C12N 15/86; C12N 7/01; C12N 5/10
[52] U.S. Cl. .................... 435/172.3; 435/235.1; 435/240.2; 435/320.1
[58] Field of Search ................ 435/172.3, 235.1, 435/240.2, 320.1

[56] References Cited

U.S. PATENT DOCUMENTS

| | | | |
|---|---|---|---|
| 4,405,712 | 9/1983 | Vande Wooude et al. | 435/5 |
| 4,738,922 | 4/1988 | Haseltine et al. | 435/69.1 |
| 5,292,662 | 3/1994 | Sandmeyer | 435/320.1 |

FOREIGN PATENT DOCUMENTS

| | | | |
|---|---|---|---|
| 0178220 | 1/1985 | European Pat. Off. | C12N 15/86 |
| 8600922 | 2/1986 | European Pat. Off. | C12N 1/00 |
| 2104901 | 7/1982 | United Kingdom | C12N 15/00 |
| 8505636 | 12/1985 | WIPO | C12P 19/34 |
| 8803563 | 5/1988 | WIPO | C12N 15/00 |
| 8803169 | 5/1988 | WIPO | C12N 15/00 |
| 8803562 | 5/1988 | WIPO | C12N 15/00 |

OTHER PUBLICATIONS

Mann, Richard, et al., "Construction of a Retrovirus Packaging Mutant and Its Use to Produce Helper–Free Defective Retrovirus." Cell 33:153–159 (1985).
Miller, A. Dusty et al., "Redesign of Retrovirus Packaging Cell Lines to Avoid Recombination Leading to Helper Virus Production." Mole. & Cell. Biol. 6:2895–2902 (1986).
Eglitis, Martin, et al., "Gene Expression in Mice After High Efficiency Retroviral–Mediated Gene Transfer." Science. 230:1395–1398 (1985).
Clark Doni J. et al., "A Yeast Sigma Composite Element, TY3, Has Properties of a Retrotransposon." J. Biol. Chem. 263:1413–1423 (1988).
Feng, Da–Fei, et al., "Progressive Sequence Alignment as a Prerequisite to Correct Phylogenetic Trees." J. Mole. Evol. 25:351–360 (1987).
Ito, Hisao, et al., "Transformation of Intact Yeast Cells Treated with Alkali Cations." J. Bacteriology. 153:163–168 (1983).
Boeke, Jef D. et al., "Ty Elements Transpose Through an RNA Intermediate." Cell. 40:491–500 (1985).
Huang, Anthony, et al., "Monoclonal Antibody Covalently Coupled with Fatty Acid: A Reagent for in Vitro Liposome Targeting." J. Biol. Chem. 255:8015–8018 (1980).
Misra, Tapan K. et al., "Avian Retrovirus pp32 DNA–Binding Protein: I. Recognition of Specific Sequences on Retro Virus DNA Terminal Repeats." J. Virol. 44:340–353 (1982).
Grandgenett, Duane P. et al., "Nuclease Mechanism of the Avian Retrovirus pp32 Endonuclease." J. Virol. 48:970–974 (1986).
Ausubel, "Oligonucleotide–Directed Mutagenesis without Phenotypic Selection." Basic Protocol. Units 8.1–8.3:8.1.1–8.3.3 (1987)
Shinnick, Thomas M. et al., "Nucleotide Sequence of Moloney Murine Leukaemia Virus." Nature 293:543–548 (1981).
Miller A. Dusty, et al., "Generation of Helper–Free Amphotropic Retroviruses that Transduce a Dominant–Acting, Methotrexate–Resistant Dihydrofolate Reductase Gene." Mole. Cell. Biol. 5:431–437 (1985).
Cone, Roger D. et al., "High–Efficency Gene Transfer into Mammalian Cells: Generation of Helper–Free Recombinant Retrovirus with Broad Mammalian Host Range." Proc. Natl. Acad. Sci. USA. 81:6349–6353 (1984).
Sandmeyer, Suzanne B. "Sigma Elements are Position–Specific for Many Different Yeast tRNA Genes." Nucl. Acid. Res. 16:1499–1515 (1988).
Shih Chu–Chih, et al., "Highly Preferred Targets for Retrovirus Integration." Cell 53:531–537 (1988).
Adams, Sally E. et al., "The Expression of Hybrid HIV: Ty Virus–like Particles in Yeast." Nature 329:68–70 (1987).
Eglitis, Martin A. "Retroviral Vectors for Introduction of Genes into Mammmalian Cells." BioTech. 6:608–614 (1988).
Fink, Gerald F. et al., "The Mechanism and Consequences of Retrotransposition." Review TIG 118–123 (1986).
Terry, Robert, et al., "Properties of Avian Sarcoma–Leukosis Virus pp32–Related Pol–Endonucleases Produce in *Escherichia coli*." J. Virol. 62:2358–2365 (1988).
Chodosh, Lewis A. et al., "A Yeast and a Human CCAAT–Binding Protein Have Heterologous Subunits That are Functionally Interchangeable." Cell 53:25–35 (1988).
Hansen, Lori J. et al., "Ty3 A Yeast Retrotransposon Associated with tRNA Genes, Has Homology to Animal Retroviruses."Mol. Cell. Biol. 8:5245–5256 (1988).

(List continued on next page.)

*Primary Examiner*—Richard A. Schwartz
*Assistant Examiner*—Philip W. Carter
*Attorney, Agent, or Firm*—Campbell and Flores

[57] ABSTRACT

The present invention provides vectors for the efficient and position-specific integration of expressible, exogenous nucleotide sequences into cellular genomes. This invention takes advantage of the discovery of a position-specific endonuclease and position-specific insertion markers for the design of said vectors. In addition, a gene comprising a recombinant nucleic acid molecule encoding a polypeptide possessing the biological activity of a position-specific endonuclease, wherein the biological activity of said endonuclease is the catalysis of position-specific insertion of genetic material carried between the position-specific integration markers, is disclosed.

17 Claims, 4 Drawing Sheets

OTHER PUBLICATIONS

Youngren, Susan D. et al., "Functional Organization of the Retrotransposon Ty from Saccharomyces Cerevisiae: Ty Protease is Required for Transportation." Mol. Cell. Biol. 8:1421–1431 (1988).

Mranyi, W. et al., "Nucleotide Sequence of a Human Retrotransposon Region Encoding a Reserve Transcriptase–like Protein." Nucl. Acids. Res. 16:7724 (1988).

Fulton, A. M. et al., "Upstream and Downstreem Transcriptional Control Signals in the Yeast Retrotransposon Ty." Nucl. Acids. Res. 16:5439–5459 (1988).

Malim, Michael H. et al., "The Production of Hybrid Ty: IFN Virus–like Particles in Yeast." Nucl. Acids. Res. 15:7571–7580 (1987).

Coney, Leslie R. et al., "Control of Yeast Gene Expression by Transpousable Elements: Maximum Expression Requires a Functional Ty Activator Sequence and a Defective Ty Promotor." Mol. Cell. Biol. 8:4009–4017 (1988).

Jacobs, E. et al., "Retrovirus–like Vectors for *Saccharomyces cervisiae*: Integration of Foreign Genes Controlled by Efficient Promoters into Yeast Chromosomal DNA." Gene 67:259–269 (1988).

Iida, Hidetoshi, "Multistress Resistance of *Saccharomyces cerevisiae* is Generated by Insertion of Retrotransposon Ty into the 5' Coding Region of the Adenylate Cyclase Gene." Mol. Cell. Biol. 8:5555–5560 (1988).

Eichinger, Daniel, et al. "The DNA Intermediate in Yeast Ty 1 Element Transposition Copurifies with Virus–like Particles: Cell–Free Ty 1 Transposition." Cell 54:955–966 (1988).

Holmes, David S. and Quigley, Michael "A Rapid Boiling Method for the Preparation of Bacterial Plasmids." Anal. Biochem. 114:193–197 (1981).

FIG. 4A
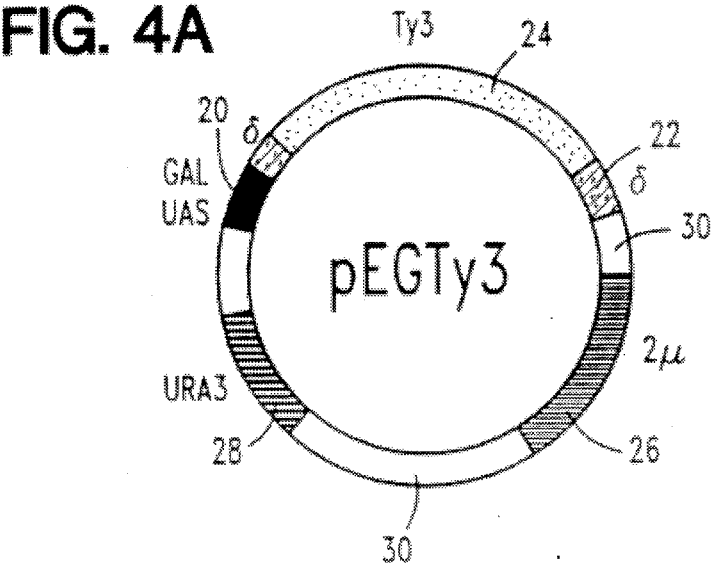
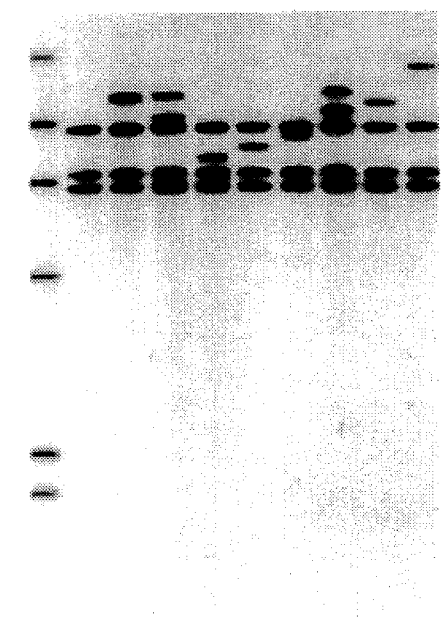
FIG.4B
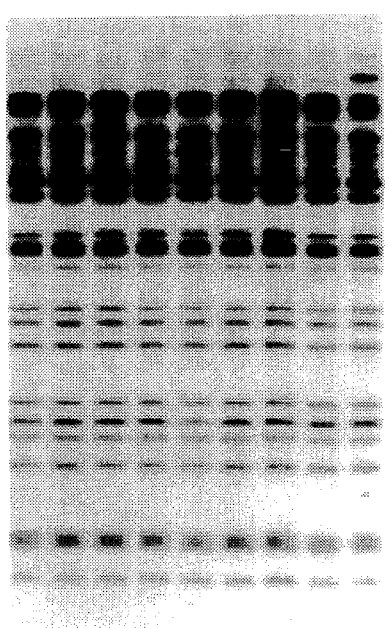
FIG.4C

```
GCA GTT ATG AGA CTA TAT CAT GAC CAT ACC TTA TTT GGA GGA CAT TTT GGT GTA ACA GTG ACC
                 15                      30                      45                      60
CTT GCG AAA ATC AGC CCA ATT TAC TAT TGG CCA AAA TTA CAA CAT TGC ATC ATA CAA TAC ATC
                 75                      90                     105                     120
AGG ACC TGC GTA CAA TGT CAA ATA CTA ATA AAA TCA CAC CGA CCA CGC TTA CAT GGA CTA TTA CAA
                135                     150                     165                     180
CCA CTC CCT ATA GCA GAA GGA TGG CTT GAT ATA TCA ATG GAT ATT GTG ACA GGA TTA CCC
                195                     210                     225                     240
CCG ACA TCA AAT AAC TTG AAT ATG ATC CTC GTC GTA GTT GAT CGT TTT TCG AAA CGC GCT CAC
                255                     270                     285                     300                     315
TTC ATA GCT ACA AGG AAA ACC TTA GAC GCA ACA CAA CTA ATA GAT CTA CTC TTT CGA TAC ATT
                330                     345                     360                     375
TTT TCA TAT CAT GGT TTT CCC AGG ACA ATA ACC AGT GAT AGA GAT GTC CGT ATG ACC GCC GAC
                390                     405                     420                     435
AAA TAT CAA GAA CTC ACG AAA AGA CTA GGA ATA AAA TCG ACA ATG TCT TCC GCG AAC CAC CCC
                450                     465                     480                     495
CAA ACA GAT GGA CAA TCC GAA CGA ACG ATA CAG ACA TTA AAC AGG TTA CTA AGA GCC TAT GCT
                510                     525                     540                     555
TCA ACC AAT ATT CAG AAT TGG CAT GTA TAT TTA CCA CAA ATC GAA TTT GTT TAC AAT TCT ACA
                570                     585                     600                     615                     630
CCT ACT AGA ACA CTT GGA AAA TCA CCA TTT GAA ATT GAT TTA GGA TAT TTA CCG AAT ACC CCT
                645                     660                     675                     690
GCT ATT AAG TCA GAT GAC GAA GTC AAC GCA AGA AGT TTT ACT GCC GTA GAA CTT GCC AAA CAC
                705                     720                     735                     750
CTC AAA GCC CTT ACC ATC CAA ACG AAG GAA CAC CAG CTA CCA GCT CAA ATC GAA ATG GAA ACT
                765                     780                     795                     810
AAT AAC AAT CAA AGA CGT AAA CCC TTA TTG TTA AAC ATA GGA GAT CAC GTA TTA GTG CAT AGA
                825                     840                     855                     870
GAT GCA TAC TTC AAG GGT GCT TAT ATG AAA GTA CAA CAA ATA TAC GTC GGA CCA TTT CGA
                885                     900                     915                     930                     945
GTT GTC AAG AAA ATA AAC GAT AAC GCC TAC GAA CTA GAT TTA AAC TCT CAC AAG AAA AAG CAC
                960                     975                     990                    1005
AGA GTT ATT AAT GTA CAA TTC CTG AAA AAG TTT GTA TAC CGT CCA GAC GCG TAC CCA AAG AAT
               1020                    1035                    1050                    1065
AAA CCA ATC AGC AGC TCC ACT GAA AGA ATT AAG AGA GCA CAC GAA GTT ACT GCA CTC ATA GGA ATA
               1080                    1095                    1110                    1125
GAT ACT ACA CAC AAA ACT TAC TTA TGT CAC ATG CAA GAT GTA GAC CCA ACA CTT TCA GTA GAA
               1140                    1155                    1170                    1185
TAC TCA GAA GCT GAA TTT TGC CAA ATT CCC GAA AGA ACA CCA TCA ATA TTA GCC AAC TTT
               1200                    1215                    1230                    1245
AGA CAA CTC TAC GAA ACA CAA GAC AAC CCT GAG AGA GAG GAA GAT GTT GTA TCT CAA AAT GAG
               1260                    1275                    1290                    1305
ATA TGT CAG TAT GAC AAT ACG TCA CCC
               1320                    1335                    1350
```

FIG. 5

POSITION-SPECIFIC INSERTION VECTORS AND METHOD OF USING SAME

This application is a continuation of application Ser. No. 07/895,333, filed Jun. 8, 1992 now U.S. Pat. No. 5,292,662, which is a continuation of application Ser. No. 07/276,201, filed Nov. 23, 1988.

BACKGROUND OF THE INVENTION

This invention relates to retrovirus vectors for gene therapy and other applications. A retrovirus vector infects cells at high efficiency and is capable of integrating a DNA copy of itself into the host genome. Such vectors are, in many ways, desirable for introduction and expression of exogenous DNA sequences in animal cells. Prolonged, stable expression of exogenously introduced genes is a requirement for experiments in animal cell culture, as well as whole-organism experiments, such as the production of transgenic mammals and human gene therapy.

One problem with retroviral vectors is that they may insert in a region of the host genome which will suppress expression of the genes carried by the vector. Position effects are known to cause wide variation in the expression of essentially identical constructs introduced into different genomic locations.

Retroviruses are several kilobase pairs (kbp) in length, and in the integrated provirus form, consist of an internal domain flanked by long terminal repeats (LTRs) of several hundred base pairs (bp). These LTRs contain promoter, polyadenylation, and termination signals which direct synthesis of the genomic RNA. The actual RNA genome contains half of the left LTR at one end (U5 at the 5' end) and half of the right LTR at the other end (U3 at the 3' end), along with a short repeat (R) present at each end. During replication, the complete LTR is regenerated at each end, to form the full-length DNA copy. See, e.g., H. E. Varmus and R. Swanstrom, *RNA Tumor Viruses*, 2nd Ed., pp. 369–512 (1984).

The internal domain contains the coding information for at least three genes: gag, pol, and env. These coincide with the first, second and third open reading frames (ORFs). The gag gene encodes structural proteins which bind to the RNA and form the nucleocapsid. The ORF abuts or overlaps that of gag, and the pol proteins are synthesized as readthrough products from the first ORF. This unusual means of limiting expression of the second ORF depends on suppression of a stop codon separating the first and second ORFs, or upon a frameshift event. The pol gene encodes a protease, a reverse transcriptase, and an endonuclease. The protease is responsible for processing of the polyprotein, while the reverse transcriptase copies the RNA genome of the retrovirus into a full-length double-stranded DNA copy. Synthesis of the first ("minus") DNA strand is primed by a tRNA which has a short region of complementarity to the retrovirus RNA. The endonuclease presumably cleaves both the DNA copy of the retrovirus at its termini, as well as the target site in the host genome. The envelope proteins encoded by the env gene are expressed from a spliced transcript.

The steps involved in the conventional production of a retrovirus vector are outlined in FIG. 1. The proteins required for virus particle formation, replication, and integration, are supplied from an integrated helper retrovirus which has a deletion in its RNA packaging signal (psi). Although the proteins encoded by the retrovirus are all required for non-defective replication-competent retroviruses, only relatively small regions, e.g., the termini, plus- and minus-strand primer binding sites, and psi, are required in cis on the RNA for it to be packaged and replicated within the retrovirus particle. These sequences, in addition to the gene of interest, are present in the retrovirus vector. DNA containing the vector sequences is transfected into the packaging line and the RNA is produced and packaged. As described above, the process of reverse transcription into DNA takes place within the virus nucleocapsid and the complete LTRs are regenerated. The outside ends of the LTR sequences, which themselves contain short inverted repeats, have been shown to be bound by the retrovirus endonuclease in vitro and to be required for integration.

For both packaging lines and vectors, murine leukemia viruses have been widely used. There are several reasons for this. First, their molecular biology is relatively well-understood. Second, they infect hematopoietic cells efficiently. Third, findings can be extended to whole animal models, and finally, amphotropic viruses are available which infect cultured cells from different mammalian species.

The murine psi-2 line was one of the first packaging lines to be developed for production of retrovirus vectors. See, e.g., R. Mann, et al., *Cell* 33: 153 (1983). The genomes of these cells have integrated copies of Moloney murine leukemia virus (MoMLV) which have deleted psi sequences. PA12 and psi-AM packaging lines are similar to psi-2 but have envelope proteins contributed from amphotropic viruses to increase host range. Because psi-2 has been shown to transmit helper virus (albeit at very low frequency), additional deficiencies have been introduced in subsequent versions of the helper viruses to further restrict the sequences which are packaged. See, e.g., A. D. Miller and C. Buttimore, *Mol. Cell. Biol.* 6: 2895 (1986).

There are now several variations of vectors in common use. One such vector, N2, is based on a murine leukemia virus and contains the complete retrovirus LTRs, the primer binding sites, the psi sequence, and a copy of the Tn5 neomycin-resistance gene (neoR) which is expressed from an internal (non-LTR) promoter. Conventional variations on this vector include the following: 1) substitution of different drug resistance markers; 2) expression of a second gene from a spliced message; and 3) modification of the LTRs to inactivate the LTR promoter at the 5' end once integration has occurred. Although these modifications do have technical advantages, they can also result in the production of decreased titers of a virus, thereby reducing their utility.

Despite the demonstrated advantages of retroviral vectors for introduction and expression of foreign genes in animal cells, problems remain with their use in human gene therapy. First, replication competent retroviruses have the ability to multiply in the host cell in which they are directed to integrate. This danger may be reduced by debilitating the vector via removal of internal sequences coding for proteins involved in packaging and replication. Use of debilitated retrovirus vectors, however, necessitates the use of helper cell lines which supply the missing functions but do not have the terminal sequences required for retroviral transposition. This raises the possibility that endogenous retrovirus transcripts from helper cells can be packaged with the vector sequences, or that vector and defective helper sequences can recombine to produce a virus capable of replication. If recombination does take place between the vector and the debilitated packaging virus, viable retrovirus may be produced which can be carried along at low frequency with the vector.

Second, retroviruses insert relatively randomly in the genome. Two problems are implicit in this property. Insertion of promoters carried on the retrovirus vector may activate cellular genes flanking the integration site. An example of the potential danger in this is activation of adjacent oncogenes. Insertion of retroviruses into coding sequences may also be deleterious. In most cases, the affected cells might simply be lost from the population; however, loss-of-function mutations may also promote oncogenesis. Thus, there are problems implicit in the relatively non-specific pattern of retrovirus insertion.

Finally, retroviral vectors inserted in different chromosomal locations are expressed at different levels. See, e.g., M. A. Eglitis, et al., *Science* 230: 1395–1398 (1985). These position effects may be attributable to the transcriptional activity of sequences flanking the insertion site. This property means that populations of cells derived from different progenitors, i.e., with vectors inserted at different positions, will have differential levels of vector expression. For example, retroviral vectors may insert in a region of the host genome which will suppress expression of the genes carried by the vector. While this may yield an "average" level of acceptable activity for gene transfers that are performed on large populations of cells, differential expression of independent insertions in transgenic animals could greatly complicate strategies designed to correct genetic defects expressed in different tissues.

Therefore, if one could design vectors which insert in a specific, innocuous location in the genome, disruption of host cell functions could be avoided. The present invention provides a heterologous vector incorporating features which allow it to integrate with position specificity, thereby providing significant advantages over current methodologies.

SUMMARY OF THE INVENTION

The present invention provides vectors for the efficient and position-specific integration of exogenous DNA into animal cell genomes. It takes advantage of our discovery of a position-specific yeast retrotransposon, Ty3, in order to design the integration vectors. See Clark, et al., "A Yeast Sigma Composite Element, Ty3, has Properties of a Retrotransposon," *J. Biol. Chem* 263: 1413– 1423 (1988), which is incorporated herein by reference. Ty3 is a yeast retrotransposon which has homology to animal retroviruses, but which inserts in the 5' flank of many different tRNA genes.

Retrotransposons belong to a class of transposable elements, which are DNA sequences. capable of movement from one position to another in the genome. Depending upon their sites of insertion, they can modify both the expression and arrangement of host genes. One class of transposable elements, which includes the retrovirus-like, retrotransposon elements of yeast, transposes through an RNA-mediated process. Retrotransposons are flanked by 4–6 bp direct repeats of target sequence. Each element is a composite consisting of an internal region of several kbp, flanked by LTRs of several hundred bp each. The ends of these LTRs are inverted repeats, up to 10 bp in length, which terminate with the conserved dinucleotides TG-CA. The LTRs contain initiation, termination, and polyadenylation signals which direct transcription of the internal coding sequences. (Clark, et al., supra.)

Studies of the mechanism of position-specific Ty3 integration and of the structure of the endonuclease which catalyzes it allow identification of the domains within the endonuclease which are responsible for catalytic function and for specificity. This information is used to engineer position-specific retrovirus vectors as outlined below. A particular objective of the present invention is to modify both the specificity and catalytic domains of the endonuclease by directed mutagenesis and to produce vectors with advantages over those which are currently available.

For the sake of clarity and simplicity, it should be remembered that, with respect to the within disclosure, the term "endonuclease" as it applies to the Ty3 endonuclease, comprises the polypeptide encoded by the gene sequence set out infra in FIG. 5 (SEQ. ID NO. 1), which polypeptide possesses position-specific endonuclease activity. The term position-specific markers shall refer to the sequences present at the outside ends of the replicated vector (or the RNA equivalent) which are required for endonuclease recognition and position-specific insertion.

The idea of specific insertion is not necessarily limited in application to retrovirus vectors. Technology for efficient integration of DNA, using engineered endonucleases, may also be used to design "streamlined" vectors in which the retroviral sequences and required retroviral proteins are minimized. For example, DNA, endonuclease and the minimal nucleocapsid core might be introduced into liposomes and targeted to a wide range of tissues by decoration with envelope proteins from various viruses, or with antibodies. The engineered endonuclease activity is therefore a critical feature of this invention. The existence of efficient, position-specific vectors will offer substantial advantages for research in animal gene expression and for the application of these findings in gene therapy.

Thus, in accordance with one aspect of the present invention, there is provided a recombinant nucleic acid sequence comprising a gene or genes encoding a desired protein, the gene(s) being flanked by the position-specific integration markers of *S. cerevisiae* Ty3. In accordance with another aspect of the invention, a position-specific endonuclease which recognizes the integration markers is provided in a vector, such as a DNA virus, an RNA virus, or a plasmid. In one embodiment, the position-specific integration marker flanking the 5' end of the nucleic acid sequence (defined for duplex DNA relative to the strand homologous to the transcript or genomic RNA) is in the following sequence: (5') TGTTGTATCT CAAAATGAGA TATGTCAGTA TGACAATACG TCACCCTGAA (SEQ ID NO. 2), and the position-specific integration marker flanking the 3' end of the replicated nucleic acid sequence is in the following sequence: (5') TATTAGGATT GTCAAGACAC TCCGATATTA CTCGAGCCCG TAATACAACA (SEQ ID NO. 3). and wherein the position-specific integration marker flanking the 5' end of an internal domain nucleic acid sequence, in the form which is expressed as a transcript, is in the following sequence: UAUUAGGAUU GUCAAGA-CAC UCCGGUAUUA CUCGAGCCCG UAAUACAACA (SEQ ID NO:14) and wherein the position-specific integration marker flanking the 3' end of the internal domain nucleic acid sequence, in the form which is expressed as a transcript, is in the following sequence: UGUUGUAUCU CAAAAUGAGA UAUGUCAGUA UGACAAUACG UCACCCUGAA (SEQ ID NO:15) and further, wherein these sequences, in the replicated full-length DNA, would be found at the 3' and 5' outside ends, respectively, as well as internally Also a part of the present invention is a transmission vector (which may be produced by the above-identified helper cell line) for inserting an exogenous gene into the genome of a target cell in a position-specific manner, wherein the vector includes an endonuclease having the position specificity of *S. cerevisiae* Ty3 endonuclease, or a nucleic acid sequence expressible in the target cell coding for the endonuclease; and an exogenous gene to be inserted in the target genome, the gene located between position-specific integration markers. In one embodiment, the gene comprises DNA. In another, it comprises RNA, and the vector further comprises proteins or nucleic acid sequences for proteins required to present the gene to the target cell. In another embodiment, the vector includes an envelope in which the endonuclease and the gene are contained. This envelope may advantageously be either a lipid vesicle or a viral envelope.

In accordance with another aspect of the present invention, there is provided a gene comprising a recombinant nucleic acid molecule encoding a polypeptide possessing the biological activity of S. cerevisiae Ty3 position-specific endonuclease, wherein the biological activity is the catalysis of position-specific insertion of genetic material carried between the position-specific integration markers of S. cerevisiae Ty3. Preferably, the endonuclease is encoded by the following sequence, or codon equivalents thereof: (5') GCA GTT ATG AGA CTA TAT CAT GAC CAT ACC TTA TTT GGA GGA CAT TTT GGT GTA ACA GTG ACC CTT GCG AAA ATC AGC CCA ATT TAC TAT TGG CCA AAA TTA CAA CAT TGC ATC ATA CAA TAC ATC AGG ACC TGC GTA CAA TGT CAA CTA ATA AAA TCA CAC CGA CCA CGC TTA CAT GGA CTA TTA CAA CCA CTC CCT ATA GCA GAA GGA AGA TGG CTT GAT ATA TCA ATG GAT TTT GTG ACA GGA TTA CCC CCG ACA TCA AAT AAC TTG AAT ATG ATC CTC GTC GTA GTT GAT CGT TTT TCG AAA CGC GCT CAC TTC ATA GCT ACA AGG AAA ACC TTA GAC GCA ACA CAA CTA ATA GAT CTA CTC TTT CGA TAC ATT TTT TCA TAT CAT GAT TTT CCC AGG ACA ATA ACC AGT GAT AGA GAT GTC CGT ATG ACC GCC GAC AAA TAT CAA GAA CTC ACG AAA AGA CTA GGA ATA AAA TCG ACA ATG TCT TCC GCG AAC CAC CCC CAA ACA GAT GGA CAA TCC GAA CGA ACG ATA CAG ACA TTA AAC AGG TTA CTA AGA GCC TAT GCT TCA ACC AAT ATT CAG AAT TGG CAT GTA TAT TTA CCA CAA ATC GAA TTT GTT TAC AAT TCT ACA CCT ACT AGA ACA CTT GGA AAA TCA CCA TTT GAA ATT GAT TTA GGA TAT TTA CCG AAT ACC CCT GCT ATT AAG TCA GAT GAC GAA GTC AAC GCA AGA AGT TTT ACT GCC GTA GAA CTT GCC AAA CAC CTC AAA GCC CTT ACC ATC CAA ACG AAG GAA CAG CTA GAA CAC GCT CAA ATC GAA ATG GAA ACT AAT AAC AAT CAA AGA CGT AAA CCC TTA TTG TTA AAC ATA GGA GAT CAC GTA TTA GTG CAT AGA GAT GCA TAC TTC AAG AAA GGT GCT TAT ATG AAA GTA CAA CAA ATA TAC GTC GGA CCA TTT CGA GTT GTC AAG AAA ATA AAC GAT AAC GCC TAC GAA CTA GAT TTA AAC TCT CAC AAG AAA AAG CAC AGA GTT ATT AAT GTA CAA TTC CTG AAA AAG TTT GTA TAC CGT CCA GAC GCG TAC CCA AAG AAT AAA CCA ATC AGC TCC ACT GAA AGA ATT AAG AGA GCA CAC GAA GTT ACT GCA CTC ATA GGA ATA GAT ACT ACA CAC AAA ACT TAC TTA TGT CAC ATG CAA GAT GTA GAC CCA ACA CTT TCA GTA GAA TAC TCA GAA GCT GAA TTT TGC CAA ATT CCC GAA AGA ACA CGA AGA TCA ATA TTA GCC AAC TTT AGA CAA CTC TAC GAA ACA CAA GAC AAC CCT GAG AGA GAG GAA GAT GTT GTA TCT CAA AAT GAG ATA TGT CAG TAT GAC AAT ACG TCA CCC (SEQ ID NO. 1). It must also be kept in mind that the foregoing sequence represents one strand, to which there is a complementary sequence.

Preferably, the position-specific integration markers flanking the 5' end of the genetic material to be inserted into the target cell genome is in the following sequence: (5') TGTTGTATCT CAAAATGAGA TATGTCAGTA TGA-CAATACG TCACCCTGAA (SEQ ID NO. 2), and the marker flanking the 3' end of the genetic material to be inserted is in the following sequence: (5') TATTAGGATT GTCAAGACAC TCCGGTATTA CTCGAGCCCG TAATACAACA (SEQ ID NO 3). Recombinant nucleic acid sequences containing these markers are also within the scope of the present invention.

The present invention further includes a modified helper cell line containing an integrated, exogenous nucleotide sequence within the cellular genome coding for the position-specific endonuclease of S. cerevisiae, and further containing, within cellular boundaries, an exogenous unincorporated nucleic acid sequence for packaging into a viral vector, comprisinq an unincorporated gene flanked on either side by marker sequences which ensure recognition by the endonuclease. The integrated, exogenous nucleotide sequence is preferably a replication-incompetent helper retrovirus (i.e-, one containing a deletion of the packaging signal). The integrated sequence preferably further comprises a nucleic acid sequence coding for a promoter-translation start region; a nucleic-acid-binding polypeptide (e.g. gag); a reverse transcriptase; and an endonuclease; and a nucleic acid sequence coding for an envelope polypeptide. In one embodiment, the endonuclease-coding sequence comprises a sequence required for the S. cerevisiae Ty3 endonuclease position-specific activity or for an endonuclease possessing the specificity domain of the S. cerevisiae Ty3 endonuclease. The helper cell line may, in one preferred embodiment, be psi-2, modified to include Ty3 sequences required for endonuclease specificity. In another embodiment, the integrated, exogenous sequence is derived from the amphotropic murine leukemia viruses.

Also included within the scope of the present invention is antibody specific for S. cerevisiae Ty3 endonuclease, and continuous cell lines producing and secreting antibody specific for S. cerevisiae Ty3 endonuclease. The present invention further provides a method for utilizing said antibody to prepare substantially pure S. cerevisiae Ty3 endonuclease.

Yet another aspect of the invention relates to a method for the construction of a modified helper cell line, comprising the steps of providing an exogenous, expressible, replication-incompetent nucleotide sequence coding for a nucleic acid-binding polypeptide, a reverse transcriptase, S. cervisiae insertion position specific endonuclease, and an envelope polypeptide; and integrating the sequence into the helper cell genome.

In accordance with still another aspect of the present invention, there is provided a method for producing transmission vectors capable of inserting specifically next to tRNA genes comprising the steps of providing helper cell line having a first exogenous, replication-incompetent nucleotide sequence coding for a nucleic acid-binding polypeptide, a nucleotide sequence coding for a polypeptide comprising a promoter-translation start region, a reverse transcriptase, an endonuclease, such as one having the insertion-position specificity of S. cerevisiae, and an envelope polypeptide, all incorporated into the genome thereof; providing within the cellular boundaries of said helper cell line a second recombinant nucleic acid sequence comprising a gene encoding a desired protein, the gene being flanked by the position-specific integration markers required by the position-specific activity of S. cerevisiae Ty3; and permitting the second recombinant nucleic acid sequence, together with nucleic-acid binding proteins, endonuclease and reverse transcriptase produced from the first nucleic acid sequence, to be packaged in said helper cell line into a transmission vector.

The present invention also provides a vector for inserting an exogenous gene into the genome of a cell in a position-specific manner, comprising: an endonuclease having the insertion position specificity of S. cerevisiae Ty3 endonuclease, or a nucleic acid sequence expressible in the cell coding for the endonuclease; and an exogenous expressible gene to be inserted in the genome of a target cell, the gene located between LTRs recognized by the endonuclease. Promoter and recognition sequences may advantageously be provided, as is well known. The vector is preferably incorporated into an envelope, such as a viral envelope or a lipid vesicle. Where the exogenous gene is RNA, the vector also includes reverse transcriptase.

Still another aspect of the present invention relates to a recombinant nucleic acid sequence comprising a gene which, when replicated, is flanked on the 5' end by the position-specific marker for S. cerevisiae Ty3 endonuclease in the following sequence: (5') TGTTGTATCT CAAAAT-GAGA TATGTCAGTA TGACAATACG TCACCCTGAA (SEQ ID NO. 2), and flanked on the 3' end by the position-specific marker for S. cerevisiae Ty3 endonuclease in the following sequence: (5') TATTAGGATT GTCAAGACAC TCCGGTATTA CTCGAGCCCG TAATACAACA (SEQ ID NO. 3). The present invention further provides a vector containing the foregoing sequences, and suggests a method for constructing said vector.

Finally, the present invention provides a method for inserting an exogenous gene into the DNA of a cell, comprising providing an exogenous gene and an endonuclease having the insertion position specificity of S. cerevisiae in the cell, wherein the exogenous gone is flanked by termini recognized by the endonuclease, so that the endonuclease cleaves the DNA in the cell adjacent to a tRNA gene and inserts the exogenous gone and the termini into the DNA at the cleavage site.

BRIEF DESCRIPTION OF THE DRAWINGS

FIGS. 4A–4C illustrate the transposition of Ty3.

FIG. 5 diagrams the nucleotide sequence (SEQ ID NO: 1) containing the gene for S. cerevisiae Ty3 position-specific endonuclease.

DETAILED DESCRIPTION OF THE INVENTION

Figure 1:
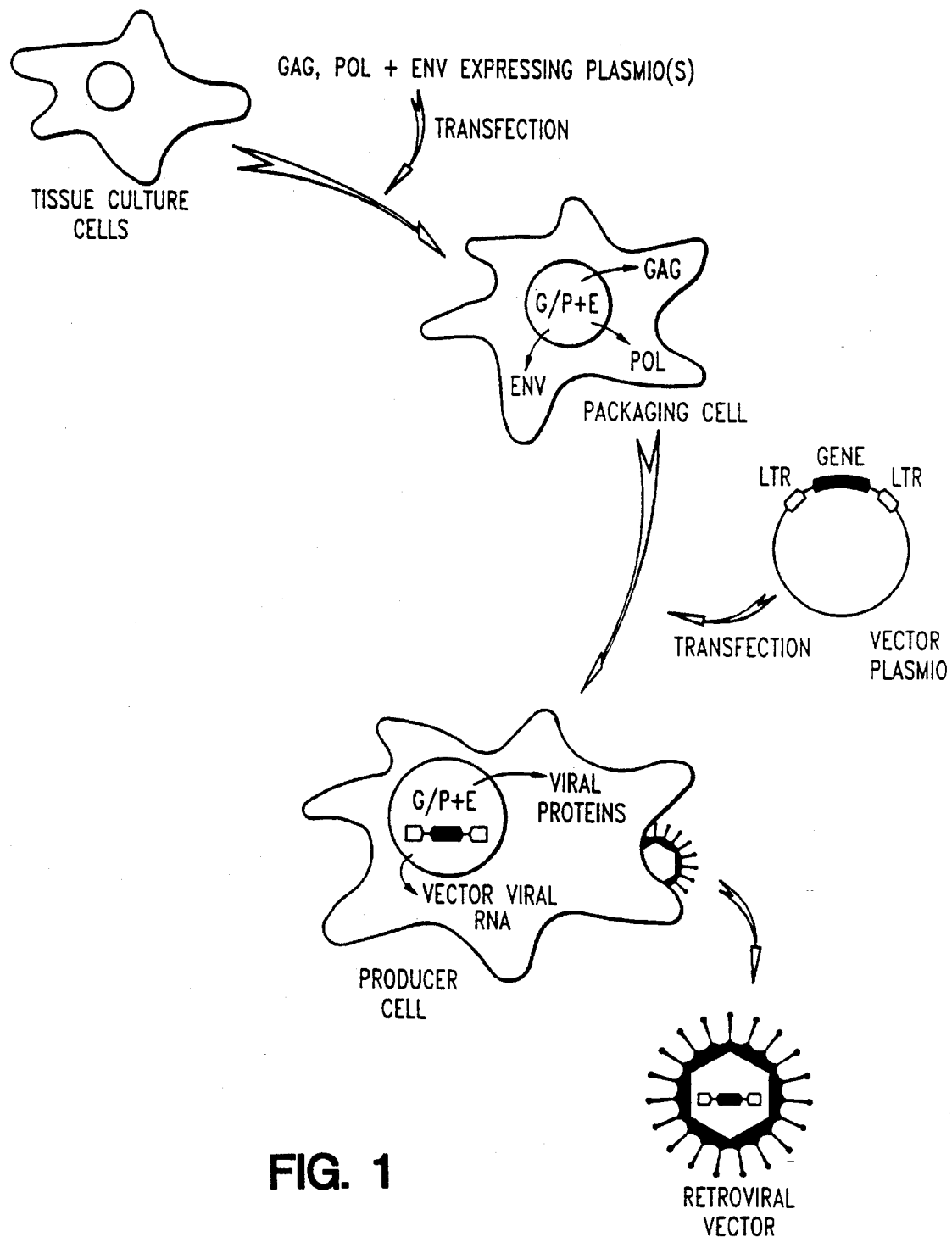
FIG. 1 diagrams the production and packaging of retrovirus vectors.
Figure 2:
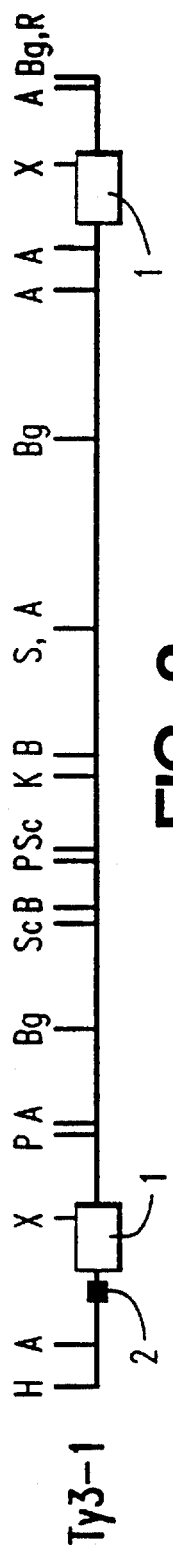
FIG. 2 illustrates the restriction site map of the cloned Ty3 element, Ty3-1.

Ty3 is a retrotransposon found in the yeast *Saccharomyces cerevisiae* which has organizational and sequence homology to animal retroviruses. (Clark, etal., supra.) Retrotransposons are retrovirus-like transposable elements which lack envelope proteins and do not have an obligatory extracellular phase. Ty3 consists of an internal domain, 4.7 kbp in length, flanked by LTRs 340 bp in length called sigma elements. FIG. 2 illustrates the restriction-site map of *S. cerevisiae* genomic fragments containing Ty3-1. The sigma elements 1 and tRNA gene 2 are indicated. Gene 2 codes for the amino acid cysteine (Cys), as shown; the direction of transcription of tRNA gene 2 is indicated by the arrow directly beneath the genes. Transcription of the Ty3 element occurs in a left-to-right direction. The kilobase (kb) scale shown at the bottom of FIG. 2 is aligned with the left ends of the upstream sigma elements. Restriction sites are abbreviated as shown. The Ty3 element shown is a composite consisting of an internal region of several kbp, flanked by LTRs of several hundred bp each. The ends of these LTRs are inverted repeats, up to 10 bp in length, which terminate with the conserved dinucleotides TG-CA. The LTRs contain initiation, termination, and polyadenylation signals which direct transcription of the internal coding sequences. (Clark, et al., supra.)

The internal domain of Ty3 contains two long ORFs. The functions encoded can be assigned based on similarity of the predicted protein sequence to sequences of retrovirus proteins. The predicted protein sequence from the first Ty3 ORF shows the presence of a conserved motif found in the retroviral nucleic acid-binding protein and encoded by the retrovirus gag gene. The second Ty3 resembles the pol gene retroviruses; it overlaps the first ORF and encodes a protease, a reverse transcriptase, and an endonuclease, in that order. A comparison of Ty3 reverse transcriptase and endonuclease protein sequences to the sequences of those encoded by Ty1 and Ty2 (two yeast retrotransposons), human immunodeficiency virus, Rous sarcoma virus, bovine leukemia virus, and MoMLV shows that the latter four have the most similarity to the Ty3-encoded proteins, and that the Ty1 and Ty2 proteins have the least similarity. Further, the identity between the reverse transcriptase (polymerase) domains of MoMLV and Ty3 is 26%.

Figure 3:
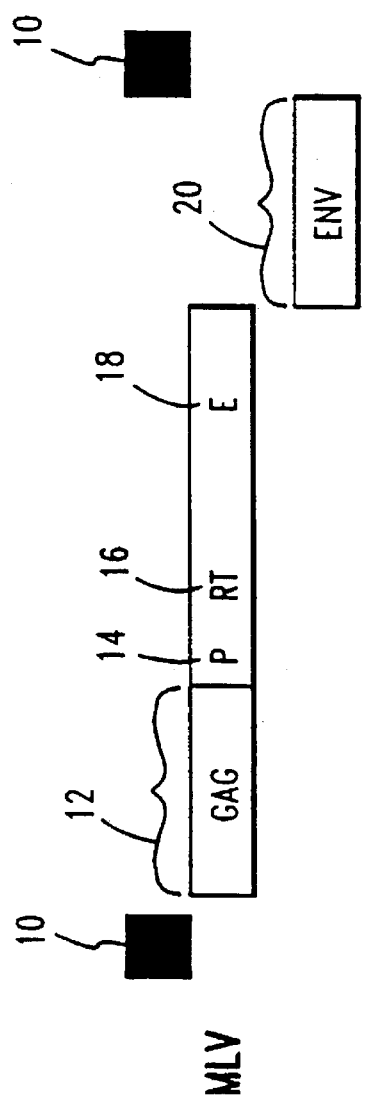
FIG. 3 illustrates the comparative structures of Ty3 and Moloney Murine Leukemia Virus (MoMLV).

FIG. 3 illustrates the overall structures of MoMLV and Ty3 in a comparative fashion. The LTRs 10, nucleocapsid proteins 12, proteases 14, reverse transcriptases 16, and endonucleases 18 are shown to be similarly aligned. The envelope protein 20 of MoMLV is also illustrated. As noted previously, retrotransposons lack the ability, generally, to synthesize envelope proteins.

Ty3 differs from retroviruses significantly in that it is extremely position-specific. There are from one to four Ty3 elements in typical haploid strains of yeast. Analysis of Ty3 elements from one strain showed that the two Ty3 elements are 16 and 17 bp from the 5' end of mature tRNA-coding sequence. Positions of Ty3 insertions can also be deduced from the positions of isolated sigma elements. These isolated elements are thought to arise from recombination between the Ty3 LTRs. They are, in a sense, "footprints" marking positions previously occupied by Ty3 elements.

In our laboratory, we have determined the DNA sequence in regions flanking 17 sigma elements; in every case, the sigma elements were within 20 bp of the 5' end of mature tRNA-coding sequence or were the tRNA gene-distal sigma LTR of a Ty3 element. We inferred that the Ty3 element is highly position specific.

Under normal conditions, Ty3 is not highly transcribed and therefore does not transpose frequently. In order to study the molecular mechanism of Ty3 transposition, we developed a system in which Ty3 transposition would occur on galactose-containing medium at high frequency. Upstream activating sequences (UAS) from the galactose-inducible yeast GAL1-10 gene were fused upstream of the Ty3 promoter. On a galactose carbon source, high levels of Ty3 transcription are induced and frequent Ty3 (1–2% of cells) transposition results.

Recombinant DNA Manipulations

Bacterial culture conditions and recombinant DNA manipulations were as described in Clark, et al., supra, and are incorporated by reference herein. Chromosomal DNA from *S. cerevisiae* strain AB972 (Dr. Maynard Olson, Washington Univ., St. Louis) was digested with EcoRI and fractionated on a 1% agazose gel. DNA fragments between 5.5 kb and 7.5 kb in length were isolated from low-gelling temperature agarose (BioRad), subcloned into the EcoRI site of pIBI21 (commercially available from International Biotechnologies, Inc. , "IBI", New Haven, Conn.), and transformed into HB101 [ (F−, hsdS20 $r_B^-$, $m_B^-$), recA13, leuB6, ara-14, proA2, lacY1, galK2, rpsL20 (Sm$^1$) , xyl-5, mtl-1, supE44, λ−]. The plasmid pIBI21 contains a cloning-region downstream of the bacteriophage T7 promoter and the IBI primer sequence., which is followed by the M13 primer sequence. The bacteriophage f1 origin of replication is present in pIBI21 and allows production of single-stranded plasmid DNA when the bacteria transformed with pIBI21 are super-infected with the helper phage M13K07 (IBI). Transformants containing the Ty3 insert were identified by colony hybridization, using a radiolabeled, internal restriction fragment as a probe. This plasmid is designated pTy3-2, which does not transpose. The Ty3 cloned previously (pSBS12; see Clark, et al., supra) is contained on a HindIII-EcoRI restriction fragment ligated into the HindIII and EcoRI sites of pIBI20, and is designated pTy3-1; Ty3-1 is capable of transposition.

In order to facilitate studies of Ty3 transposition, the GAL1-10 upstream activating sequence (UAS) was fused upstream of the TATAA sequences of Ty3-1 and Ty3-2. In the first step of the construction, a 276-bp AluI fragment (nucleotide positions 123-398 in sigma) containing the Ty3 TATAA sequences and transcription start site was subcloned into the SmaI site of the pIBI20 polylinker. This construct was cleaved with SalI in the polylinker and with XhoI in the downstream end of the sigma element to produce a sigma promoter fragment with XhoI-compatible ends. This fragment was then inserted into the XhoI site downstream of the GAL1-10 UAS in a derivative of pHZ18 to produce pALG28. The HindIII-XhoI fragment from pALG28 containing the yeast URA3 gene and the GAL1-10 UAS-sigma promoter fusion was cloned into a site in pTy3-1 or pTy3-2 created by complete HindIII digestion and partial XhoI digestion. Screening by restriction digestion of these constructs identified plasmids pGTy3-1 and pGTy3-2 in which the GAL1-10 UAS-sigma promoter is fused to the Ty3-t or Ty3-2 internal domain. pGTy3-1 and pGTy3-2 were converted to high-copy yeast vectors, pEGTy3-1 and pEGTy3-2, respectively, by insertion of the 2.2 kb EcoRI fragment from the yeast 2 micron episome.

Nucleotide Sequence Strategy

The directed-deletion strategy of Henikoff was used to create overlapping subclones for sequence analysis of the non-coding strand of Ty3-1 by the dideoxy-chain termination method. (See S. Henikoff, *Gene* 28: 351-359 (1984).) Single-stranded templates were made by superinfection of the pTy3-containing bacterial host NM522 [(Δlac-proAB), thi, hsdΔ5, sup5, supE, (F', proAB, lacI$^q$ZΔM15)], with the helper phage M13K07, and were used for the sequence reactions.

The restriction enzymes AluI, RsaI and Sau3A, which cut frequently within the Ty3-1 sequence, were used to make random subclones of suitable length for sequence analysis of the coding strand. Small-scale preparations of this DNA were obtained with the boiling method of Holmes and Quigley. (See D.S. Holmes and M. Quigley, *Anal. Biochem.* 114: 193-197 (1981).) Sequences of these inserts were determined from double-stranded plasmids in polymerass reactions primed with the M13 universal or IBI reverse sequencing primers and using the dideoxy-chain termination method. All sequence analysis used the sequenase enzyme (United States Biochemical Corp.) and [$^{35}$S]dATP (1000 Ci/mmol.; Amersham). Six synthetic oligonucleotides (Operon Technologies, Inc.) which hybridize to Ty3-1 sequence were used to allow analysis of remaining regions. The nucleotide sequence was compiled, edited and translated using the DNA sequence analysis programs of Dr. A. Goldin and Dr. G. Gutman (University of California, Irvine). Comparisons with the GenBank Nucleic Acid Database and NBRF Protein Data Base were made with the use of the University of Wisconsin Genetics Computer Group programs on a VAX computer. The amino acid comparisons of the reverse transcriptase and endonuclease were generated with the progressive alignment programs of Feng and Doolittle on a VAX computer. D. Feng and R. Doolittle, *J. Mol. Evol.* 25: 351-360 (1987). Of course, other known sequence analysis techniques could be used in a similar manner- to generate comparable data.

Transposition

Yeasts were cultured according to standard methodology. Strains yVB109 (MATα, crplα901, ura3-52, his3-200, ade2-101, lys2-1, leul-12, can1-100) and yVB110 (produced in our lab) were transformed with plasmid pEGTy3-1 or pEGTy3-2 by a modification of the procedure of Ito, et al., in *J. Bacteriol.* 153: 163-168 (1983). The strain yVB110 is an isogenic derivative of yVB109, from which the three endogenous Ty3 elements have been serially deleted. Three strains from which different Ty3 elements were deleted were obtained by URA3 disruption of individual Ty3 elements, followed by selection on 5-fluoro-orotic acid (5FOA)-containing medium for colonies which were ura3-. Strains containing multiple Ty3 deletions were derived by standard genetics. yVB110 transformants containing the inducible plasmids were selected on synthetic complete (SC) medium, minus uracil, on the basis of the uracil phototrophy conferred by the plasmid. The yVB110 transformants were streaked onto the same medium or onto that medium with 2% galactose substituted for glucose as a carbon source and incubated at 23° C. or 30° C. for 10 days. At the end of that time, ten colonies from each condition were streaked for single colonies on YPD. Fifty isolates representing each original colony were patched onto 5FOA-containing medium in order to select cells which had lost the URA3 plasmid marker. These cells were streaked onto nitrocellulose filters on YPD medium and grown approximately 14 hours. Filters were processed and hybridized as described previously. The probe was a radiolabeled fragment from the internal domain of Ty3. Strain yVB109 was similarly transformed and grown under inducing and noninducing conditions. Single colonies were isolated and cured of the plasmid as described above.

Genomic DNA for Southern blot analysis was prepared according to the method of Boeke et al., as described in Boeke, et al., *Cell* 40: 491-500 (1985). DNA for the analysis displayed in FIG. 4 (B and C) was prepared from different clonal isolates of a galactose-grown yVB109-pEGTy3-1 transformant. A total of 230 colonies were screened in 24 DNA preparations each representing groups of 8-10 colonies. Genomic DNA from these pooled cultures was isolated, digested with EcoRI, fractionated by electrophoresis in 0.8% agarose buffered in TBE (2.5 mM EDTA, 45 mM borate, and 133 mM Tris-HCl, pH 8.3), and transferred to nitrocellulose by the method of Southern. Nitrocellulose-bound DNA was hybridized and filters were washed as described in Clark, et al. (supra 1988), and exposed to Kodak XAR-5 film in the presence of a Cronex Quanta-III Intensifying Screen (DuPont) at −70° overnight. DNA was also prepared and analyzed in the same way from individual colonies which contributed to pools that showed evidence of Ty3 rearrangements. In this way, clonal isolates were identified which are homogeneous with respect to the presence of a new Ty3-hybridizing fragment. DNA from some of these was analyzed by hybridization to Ty3-specific and sigma-specific probes (see FIG. 4).

FIG. 4(A) illustrates donor plasmids containing galactose-inducible Ty3-1 and Ty3-2 sequences, which were constructed as described above and are shown generalized as pEGTy3. Yeast sequences marked are: GAL1-10 UAS, 20 (solid); sigma elements, 22 (lines and stippling); Ty3 internal domain, 24 (dark stippling); 2-micron plasmid replication sequences, 26 (thin lines); and UEA3 sequences, 28

(thick lines). *E. coli* sequences, ori and AmpR, are also shown, 30 (open spaces). Scale is approximate.

Construction of Vectors

Vectors may be constructed utilizing the position-specific endonuclease of *S. cerevisiae* using any of the well-known vector construction techniques. These techniques, however, are modified to the extent that the gene to be inserted into the genome of the host cell is flanked on either side by the marker sequences discussed herein, and the position-specific endonuclease disclosed herein that recognizes those markers must also be provided in the host cell. The position-specific endonuclease may be provided directly in the cell in its polypeptide form, or alternatively, it may be provided in the cell in the form of an expressible nucleotide sequence, either RNA or DNA, in accordance with techniques recognized in the art.

The vector itself may be of any suitable type, such as a viral vector (RNA or DNA), naked straight-chain or circular DNA, or a vesicle or envelope containing the nucleic acid material and any polypeptides that are to be inserted into the cell. With respect to vesicles, techniques for construction of lipid vesicles, such as liposomes, are well known. Such liposomes may be targeted to particular cells using other conventional techniques, such as providing an antibody or other specific binding molecule on the exterior of the liposome. See, e.g., A. Huang, et al., *J. Biol. Chem.* 255:8015–8018 (1980).

The *S. cerevisiae* position-specific endonuclease may be directly obtained by expressing a gene having the nucleotide sequence set forth in FIG. 5, or codon equivalents thereof. A promoted gene coding for this endonuclease may be expressed in any suitable expression system. Thus, it may be incorporated into a plasmid with an appropriate promoter and expressed in *E. coli*, using conventional techniques, and then may be purified using antibodies against that endonuclease. However, in a preferred embodiment (and as exemplified herein), the endonuclease gene is expressed in a helper cell line having the gene coding for the endonuclease incorporated into the genome thereof as part of an incorporated viral sequence. The helper cell line then packages an exogenous nucleotide sequence, comprising a promoted gene of interest flanked by marker sequences recognized by the position-specific endonuclease, into an RNA or DNA vector. These viral vectors will further include the position-specific endonuclease itself, and in the case of an RNA virus, the viral envelope will further include reverse transcriptase.

Thus, in practicing the present invention, any of the well known transmission vector synthesis techniques may be used, the only difference being the substitution of the *S. cerevisiae* Ty3 endonuclease for the conventional endonuclease, and the use of marker sequences recognized by the new endonuclease to flank the genetic material to be inserted into the host genome.

The marker sequences to be used may comprise, on the 5' end, the 500 base pairs immediately adjacent to the *S. cerevisiae* Ty3 retrotransposon internal domain, preferably the 50 base pairs most immediately adjacent to said domain, and most preferably the 25 base pairs most adjacent thereto. Similarly, on the 3' end of the gene to be inserted, the marker sequence may comprise the 500 base pairs immediately adjacent to the Ty3 retrotransposon internal domain, more preferably the 50 base pairs immediately adjacent thereto, and most preferably the 25 base pairs most immediately adjacent thereto. The minimum amount of genetic material comprising the essential marker sequences for the 5' and 3' sides of the gene to be inserted may be determined in accordance with Example 4. Moreover, the procedures of Examples 1–3 may be used to determine the minimal amount of the nucleotide sequence set forth in FIG. 5 that is necessary to provide the position-specific activity of the *S. cersvisiae* Ty3 endonuclease.

In one particularly preferred embodiment of the invention, the vector envelope includes not only the Ty3 endonuclease, but also the entire polypeptide expression product of the first and second ORFs of Ty3-1.

Alternatively, it is believed that some of the conventional retroviral marker sequences will be recognized by the position-specific endonuclease of the present invention. Such ether markers may be readily identified by a simple screening technique, by introducing nucleotide sequences comprising a marker gene (such as neoR) flanked by the marker sequence to be screened into a helper cell line of the present invention, then attempting to transfect another cell line with resulting viral vectors (if any) and screening for transformed cells. Any resulting transformed cells may be further analyzed to determine the location of insertion of the marker gene, as discussed in conjunction with Example 5.

Antibody Production

Antibodies against the *S. cerevisiae* Ty3 endonuclease may be obtained by immunizing an animal, particularly a mammal such as a rabbit or mouse, with *S. cerevisiae* Ty3 endonuclease, harvesting antibody-producing cells from the immunized animal, fusing the cells with I cultured immortalized cells to form hybrid cells, selecting hybrid cells which produce antibodies specific for *S. cerevisiae* Ty3 endonuclease, and harvesting antibodies from the hybrid cells.

Techniques for producing monoctonal antibody-producing cell lines in this manner are well known; one such methodology is that of Kohler and Milsrein, *Nature* 256: 495–497 (1975). Alternatively, serum from the immunized animal may be utilized as a source of polyclonal antibody against the endonuclease. Example 6 provides a description of antibody production methodology. The antibodies thus produced may in turn be utilized to purify the endonuclease on a production scale, and may be particularly useful in providing purified endonuclease for incorporation into liposome vesicles.

EXAMPLE 1

Identification of amino and carboxy termini of the Ty3 endonuclease.

The Ty3 endonuclease is the apparent determinant of Ty3 position specificity. In retroviruses, the endonuclease is synthesized as part of the gag-pol fusion protein and is cleaved out by action of the retrovirus protease. The region which encodes this protein has been identified by computer translation of the Ty3 DNA sequence, and alignment of that protein sequence with retrovirus endonuclease sequences has been performed. Large-scale purification of the endonuclease using known techniques confirms the size of the Ty3 endonuclease and the positions of its termini in the coding sequence. Recombinant constructions are available to overproduce the endonuclease in bacteria and in yeast, and antibodies to peptides representing portions of the endonuclease are available to monitor the purification of the endonuclease.

The purified protein is tested for binding to Ty3 termini and DNA-nicking activity as described for retrovirus endonucleases (e.g., Misra, et al., *J. Virol.* 44: 330–343 (1982) and Grandgenett, et al., *J. Virol.* 58: 970–974 (1986)). The purified endonuclease may then be subjected to amino-terminal sequence analysis. Several rounds of Edman degradation are usually sufficient to identify the amino terminus when these results are compared to the DNA sequence. The carboxy terminus is determined by carboxypeptidase Y digestion.

EXAMPLE 2

Olignucleotide—directed mutagenesis

The protein domain or domains which determine Ty3 insertion specificity reside within the endonuclease, which is responsible for insertion. We have undertaken intensive oligonucleotide-directed mutagenesis in order to delineate domains which confer the position-specificity. Using this technique, we introduced single copies of a unique restriction site across the endonuclease coding region, every several codons (approximately 30). Oligonucleotide mutagenesis techniques are well known in the art and are described at length in the following handbook: F. M. Ausubel, et al., Eds., *Current Protocols in Molecular BioloGy* (John Wiley & Sons, 1987). This approach yields mutations which are readily identifiable in vitro, and which can be combined later to form various deletion mutations or to generate "specificity cassettes" for introduction into animal retrovirus-coding sequences. Although the oligonucleotide approach is somewhat tedious, it has a high probablity of success, even though the effect on Ty3 transposition of a mutation within the specificity domain is not predictable.

A Ty3 transposition assay for testing the effects of oligonucleotide mutations on in vivo transposition may be performed according to the following procedure, or variants thereof, as required: A his3-, ura3- yeast strain is transformed with a plasmid carrying a marked (HIS3), galactose-inducible Ty3 element. The strain will also be transformed with a galactose-inducible copy of the Ty3 element which has the mutated endonuclease-coding region.

The doubly-transformed yeast is grown on galactose to induce Ty3 transposition. Cells are then cured of the URA3-marked plasmid by growth on 5-fluoro-orotic acid (5FOA). Transposition is measured by the frequency of colonies which have lost the marked plasmid (urz3-) but which can grow on medium lacking histidine. Such cells have acquired genomic HIS3 sequences and have thus undergone transposition events. A survey of the data produced shows which regions in the endonuclease are required for integration.

EXAMPLE 3

Assay Procedures

One way to monitor endonuclease activity is via testing its ability to specifically nick its presumed targets, which are the Ty3 termini and a tRNA gene target. The conditions under which specific DNA nicking at the ends of the LTRs and at a target tRNA.gene are maximal may be determined by standard biochemical procedures, such as those described in Grandgenett, et al., supra.

A simple way to follow protein-DNA interaction is to monitor binding of labeled, native DNA to nitrocellulose in the presence of the protein under examination. Because proteins adhere to nitrocellulose and native double-stranded DNA does not, protein-DNA interactions can be followed by such an assay. Alternatively, a gel-retardation assay may be used to follow interactions of proteins and DNA sequences, via standard procedures such as those set out in Ausubel, et al., supra.

EXAMPLE 4

Identification of Ty3 terminal sequences required for transposition

Almost all transposable elements, including integrated (retro)proviruses, have inverted-repeat termini. The actual terminal region required for integration includes these inverted repeats. The required region has been defined for retroviruses by deletion analysis and has been shown to bind the retrovirus endonuclease in vitro. The terminal region of the Ty3 element required in cis for position-specific transposition is defined by nested deletions starting within the sigma elements and going toward the outside ends. The mutations may be made very efficiently with a combination of oligonucleotide mutagenesis and Bal31 digestion. The activity of the deleted Ty3 elements is tested, as described above for endonuclease mutations, by marking the deleted Ty3 with a HIS3 insertion and assaying for its ability to integrate when complemented in trans. The minimal termini required for position-specific integration are thereby deduced.

EXAMPLE 5

Construction of a position-specific heterologous vector for use in animal cells I. Modification of Helper Virus In order to alter the specificity of a helper virus, such as the Moloney helper virus, to that of Ty3, two kinds of rearrangements are necessary. First, the endonuclease coding sequence from Ty3 must be inserted into the helper virus. This may be accomplished as follows.

The endonuclease-coding sequence from Ty3 is isolated on a BamHI restriction fragment. The endonuclease-coding sequence in Ty3 is not flanked by BamHI sites, so these are introduced via oligomutagenesis. (See F. M. Ausubel, et al., Eds., supra.) A single-stranded Ty3-1 element from the clone pEGTy3-1 is mutagenized successively with two different oligonucleotides in order to make the necessary changes. The oligonucleotides are displayed infra. It must be emphasized-that these oligonucleotide sequences are complementary, rather than identical to the Ty3-1 plus (+) strand sequence. The altered positions are indicated via underlining and boldface; numbers in parentheses are relative to the Ty3-1 plus-strand sequence:

(1) 5' (3800) CAGTCTCATAACTGCGGATCCTTGTTT-TATTGG (3768) 3' (SEQ ID NO. 4)

(2) 5' (5140) CGTTCAGGATCCCGTATTGTCATACT-GAC (5112) 3' (SEQ ID NO. 5)

A region containing a large portion of the helper virus endonuclease coding sequence should similarly be flanked by engineered BamHI sites. The virus sequence we mutagenize, i.e., MoMLV, is that of the psi minus helper virus. The coordinates given herein are relative to the sequence of the RNA genome as shown in the original sequence analysis of MoMLV (see Shinnick, et al., *Nature* 293: 543–548 (1981). The second set of mutations is as follows:

(3) 5' (4761) CAAAAGTAAAGGATCCAGGCATCA-CAGG (4734) 3' (SEQ ID NO. 6)

(4) 5' (5458) ATGTCAGGGTCAGGGGATCCTA-CAAGGGGCGGGGG (5424)3' (SEQ ID NO. 7)

When both sets of mutations have been introduced and confirmed by restriction digestion and nucleotide sequence analysis, the BamHI restriction fragment containing the endonuclease-coding region from Ty3-1 will be substituted for the BamHI restriction fragment containing a large portion of the endonuclease-coding region from MoMLV. This may be performed by restriction digestion, isolation of the appropriate fragments by agarose gel electrophoresis, and ligation of the Ty3 endonuclease-coding fragment into the MoMLV vector BamHI site. This is standard technology, as described in Ausubel, supra.

The helper virus is constructed as above and subsequently integrated into a cell line as described previously in numerous references. See, e.g., Mann, et al., *Cell* 33:153 (1983); Miller, et al., *Mol. Cell. Biol.* 5: 431 (1985); and Cone and Mulligan, *Proc. Natl. Acad. Sci.* 81:6349 (1984).

The second rearrangement involves the substitution of the substrate recognition region for the Ty3 endonuclease for the inverted repeats which supply the termini of the vector virus—in this instance, a MoMLV vector. For example, such a vector may contain a gene of interest replacing the N2 protein coding region. Essentially, the procedure is as follows. Small deletion mutations are introduced, removing the regions from which the outside ends are created for the vector virus. These mutations simultaneously remove the inverted repeat sequences from the MoMLV vector 5' and 3' LTR internal termini and create a restriction site where the Ty3 inverted repeat termini can be inserted. The first oligonucleotide given creates an XmaI site (CCCGGG). The second oligonucleotide given creates an ApaI site (GGGCCC). The coordinates of these mutations introduced for the MoMLV vector are the same as above (i.e., relative to the published sequence of the virus rather than a current vector). The Ty3 terminal sequences to be introduced are quite short and are preferably supplied as synthetic double-stranded oligonucleotides with terminal extensions that are compatible with the newly-created MoMLV vector restriction sites. The oligonucleotides which are used to create the mutations in the Moloney genome are given in the strand complementing the plus (+) strand sequence. Changed nucleotides are shown via underlining and boldface; the deleted region is indicated with a hyphen (-).

The helper or packaging line has the Ty3 endonuclease substituted for that of the retrovirus. The vector virus expressed from the helper packaging line will be vector nucleic acid (Ty3 termini) packaged by the helper virus proteins, and includes the Ty3 endonuclease polypeptide.

The vector and packaging lines described above are first tested for ability to produce virus capable of replication and position-specific integration. For example, a hoeR-marked N-2 vector modified so that the termini of the replicated virus are compatible with the Ty3 endonuclease may be transfected into a packaging line containing the integrated helper virus with the substituted endonuclease-coding sequences. Vector virus with Ty3 terminal sequences, packaged in particles or vesicles containing Ty3 endonuclease are harvested from the packaging line and then used to infect target cells. These target cells are then challenged by neomycin analogue selection to identify transformants.

Animal cell clones which are neomycin resistant, for example, are when screened for position-specific integration of the vector sequences. Restriction fragments containing vector-genome junctions are amplified by the polymerase chain reaction (PCR) and subcloned for DNA sequence analysis. A large number of integrants can also be screened to determine whether integration was position-specific for a tRNA gene by hybridizing the in vitro-amplified DNA to orobes made from total tRNA.

(5)  5' (141) CCCGGACGAGCCCCC-GGGGACGGGTAG (120) 3'    (SEQ ID NO. 8)
              XmaI (6)  5' (7843) GCCAAAGCCTACAGGG-CCCCCCTTTTTCTGG (7801) 3'    SEQ ID NO. 9)
               ApaI

The oligonucleotides with the Ty3 ends are given infra. These "cassettes" am inserted in the restriction sites shown above at the positions of the deleted Moloney vector inverted terminal repeats. Cassette 7 is inserted in the XmaI site of 5, whereas cassette 8 is inserted in the ApaI site of 6.

EXAMPLE 6

Antibody Production

Purification of the polypeptide produced by the *S. cerevisiae* Ty3 endonuclease coding sequence may be accom- (7)  5'   CCGGTATTACTCGACCCGTAATACAACACC  3'      (SEQ ID NO. 10)
     3'        ATAATGAGCTGGGCATTATGTTGTGGGGCC  5' (SEQ ID NO. 11)

(8)  5'   GGCCTGTTGTATCTCAAAATGAGATATGT  3'       (SEQ ID NO. 12)
     3'        ACAACATAGAGTTTTACTCTATACACCGG  5'  (SEQ ID NO. 13)

It should be noted that the yeast cultures and clones utilized herein are maintained in a private deposit at the University of California at Irvine. Alternatively, DNA having the sequence illustrated in FIG. 5 may be readily synthesized—via use of an automated nucleotide sequence construction device, for example—and then, that sequence may be readily inserted into the helper cell genome as described.

II. Modification of a Helper Cell Line

A cell line is then modified into a "helper" or "packaging" line, via the introduction of a plasmid or plasmids encoding the retroviral structural genes gag,pol, and env, as well as replacing retroviral endonuclease with Ty3 endonuclease as described. Next, the packaging line, for example, psi-2, is modified by insertion of a "cassette"—i.e., a plasmid carrying a cloned retrovital vector—such as one with termini recognized by the Ty3 endonuclease. The sequences introduced into the helper virus can include most of the Ty3 endonuclease or simply the specificity domain. The polypeptide—i.e., the Ty3 endonuclease itself—is associated with the vector virus.

plished using antibodies to the cloned endonuclease. Antibodies may be polyclonal, and raised in animals such as rabbits or goats by conventional immunization, or monoclonal, produced by the hybridoma technique developed by Kohler and Milsrein, *Nature* 256: 495–497 (1975).

For example, Male New Zealand white rabbits are used (albeit other genera and species may be appropriate and useful). Immunization is achieved, for example, by using Freund complete adjuvant in which the whole cells of the microorganism used are derived from the same cultures as were used to prepare a given cell sonic extract antigen. Thus, a portion of washed packed bacilli is suspended in 10 volumes of distilled water and steamed for 20 minutes. After centrifugation, the supernatant is discarded and cells are resuspended in water and steamed again for 20 minutes. The cells are again separated by centrifugation and resuspended in water to yield a suspension corresponding to 15 mg/ml (dry weight). A 6-ml volume of the crude soluble protein antigen (1 mg of protein per ml of phosphate-buffered saline) is mixed with 6 ml of incomplete Freund adjuvant (Difco, Detroit, Mich.) at 0.4 ml of homologous whole cell adjuvantsuspension and converted to a homogeneous paste by repeated flushing through a 20-gauge needle. The initial inoculum consists of 1.0 ml into each of 4 subcutaneous sites and 0.1 ml into each of 2 intradermal sites. Animals are boosted after the first five weeks with 1 ml in each of two subcutaneous sites, and thereafter at 4–5 week intervals with 0.1 ml intravenously and 0.4 ml subcutaneously.

Working samples of serum are derived from blood drawn one week after each boost.

The Ty3 endonuclease sample may be partially purified, by common protein fractionation procedures. A portion of this enzyme preparation is then used to immunize animals by standard procedures. The serum is tested for the desired antibodies to the enzyme batch that induced it, i.e., the homologous antigen. The free antibody globulin is separated from any seroprecipitate and/or immune complex by ion exchange chromatography, or other suitable technology.

The antibody is then tested to establish its potency against homologous enzyme/antigen. Alternatively, monoclonal antibodies may be produced from the endonuclease. Methods for preparation of monoclonal antibodies against an identified antigen are well known.

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All alterations which come within the meaning and range of equivalency of the claims are to be embraced within their scope.

What is claimed is:

1. A helper virus comprising a recombinant nucleic acid sequence encoding a polypeptide having the biological activity of *S. cerevisiae* Ty3 position-specific endonuclease, wherein said biological activity is the catalysis of position-specific integration of a nucleicacid sequence.

2. A helper cell line having integrated therein the helper virus of claim 1.

3. The modified helper cell line of claim 2, wherein the integrated helper virus is replication-incompetent.

4. The helper cell line of claim 2, containing an unincorporated recombinant nucleic acid sequence operatively linked to the endonuclease recognition sequence of *S. cerevisiae* Ty3.

5. The helper cell line of claim 2, further comprising a nucleic acid sequence encoding a reverse transcriptase and a nucleic acid sequence encoding an envelope polypeptide.

6. The helper cell line of claim 2, wherein said helper virus is psi⁻.

7. The helper cell line of claim 2, wherein said helper virus is a retrovirus.

8. The helper cell line of claim 7, wherein said retrovirus is a murine retrovirus.

9. The helper cell line of claim 8, wherein said murine retrovirus is Moloney murine leukemia virus.

10. The helper cell line of claim 4, wherein the endonuclease recognition sequence flanking the 5' end of the internal domain nucleic acid sequence, in the form which is expressed as a transcript, is in the following sequence:

UAUUAGGAUU GUCAAGACAC UCCGGUAUUA CUCGAGCCCG UAAUACAACA (SEQ ID NO: 14)

and wherein the endonuclease recognition sequence flanking the 3' end of the internal domain nucleic acid sequence, in the form which is expressed as a transcript, is in the following sequence:

UGUUGUAUCU CAAAAUGAGA UAUGUCAGUA UGACAAUACG UCACCCUGAA (SEQ ID NO: 15)

and further, wherein the endonuclease recognition sequences, in a replicated full-length DNA, would be found at the 3' and 5' outside ends, respectively, as well as internally.

11. A recombinant nucleic acid sequence encoding the endonuclease recognition sequence on the 5' end of *S. cerevisiae* Ty3 in the following sequence: TGTTGTATCT CAAAATGAGA TATGTCAGTA TGACAATACG TCACCCTGAA (SEQ ID NO. 2); and on the 3' end of *S. cerevisiae* Ty3 in the following sequence: TATTAGGATT GTCAAGACAC TCCGGTATTA CTCGAGCCCG TAATACAACA (SEQ ID NO. 3).

12. A transmission vector capable of inserting a recombinant nucleic acid sequence into the genome of a cell in a position-specific manner, comprising:

a. a polypeptide having the biological activity of *S. cerevisiae* Ty3 position-Specific endonuclease; and b. the recombinant nucleic acid sequence, wherein said recombinant nucleic acid sequence is operatively linked to the endonuclease recognition sequence of said endonuclease.

13. The transmission vector of claim 12, wherein said recombinant nucleic acid sequence comprises DNA.

14. The transmission vector of claim 12, wherein said recombinant nucleic acid sequence comprises RNA, wherein said vector further comprises reverse transcriptase.

15. The transmission vector of claim 13 or 14, further comprising an envelope in which said endonuclease and said recombinant nucleic acid sequence are contained.

16. The transmission vector of claim 13 or 14, further comprising a lipid vesicle in which said endonuclease and said recombinant nucleic acid sequence are contained.

17. A method for integrating a recombinant nucleic acid sequence into the DNA of a cell in a position-specific manner, comprising:

introducing the recombinant nucleic acid sequence and an endonuclease having the biological activity of *S. cerevisiae* Ty3 position-specific endonuclease into said cell, wherein said recombinant nucleic acid sequence is operatively linked to the endonuclease recognition sequence of said endonuclease, so that said endonuclease cleaves said DNA in a position-specific manner and integrates said recombinant nucleic acid sequence and said endonuclease recognition sequence into said DNA at the cleavage site.

* * * * *

UNITED STATES PATENT AND TRADEMARK OFFICE
CERTIFICATE OF CORRECTION

PATENT NO. : 5,482,853
DATED : January 9, 1996
INVENTOR(S) : Suzanne B. Sandmeyer It is certified that error appears in the above-indentified patent and that said Letters Patent is hereby corrected as shown below:

In column 1, line 44, please insert --pol-- before "ORF".

In column 2, line 57, please delete "retrcviral" and replace therefor with --retroviral--.

In column 3, line 48, please delete "sequences.capable" and replace therefor with --sequences capable--.

In column 4, line 47, please delete "TCCGATATTA" and replace therefor with --TCCGGTATTA--.

In column 4, line 48, please delete ".3)." and replace therefor with --.3)--.

In column 4, line 61, please insert --.-- after internally.

In column 5, line 31, please delete "TTT CGA TAC ATT TTT TCA TAT CAT GAT TTT CCC" and replace therefor with --TTT CGA TAC ATT TTT TCA TAT CAT GGT TTT CCC--.

In column 7, line 25, please delete "gone" and replace therefor with --gene--.

In column 7, line 28, please delete "gone" and replace therefor with --gene--.

In column 7, line 49, please delete "(Clark, etal." and replace therefor with --(Clark, et al.--.

UNITED STATES PATENT AND TRADEMARK OFFICE
CERTIFICATE OF CORRECTION

PATENT NO. : 5,482,853
DATED : January 9, 1996
INVENTOR(S) : Suzanne B. Sandmeyer It is certified that error appears in the above-indentified patent and that said Letters Patent is hereby corrected as shown below:

In column 8, line 9, please delete "Ty3 resembles" and replace therefor with --Ty3 ORF resembles--.

In column 8, line 60, please delete "agazose" and replace therefor with --agarose--.

In column 9, line 2, please delete "sequence.," and replace therefor with --sequence,--.

In column 9, line 20, please delete "Smal" and replace therefor with --SmaI--.

In column 9, line 23, please delete "Xhoi" and replace therefor with --XhoI--.

In column 9, line 55, please delete "polymerass" and replace therefor with --polymerase--.

In column 10, line 10, please delete "crplx901" and replace therefor with --trplx901--.

In column 10, line 67, please delete "UEA3" and replace therefor with --URA3--.

In column 11, line 6, please delete "These" and replace therefor with --Those--.

In column 11, line 67, please delete "cersvisiae" and replace therefor with --cerevisiae--.

UNITED STATES PATENT AND TRADEMARK OFFICE
CERTIFICATE OF CORRECTION

PATENT NO. : 5,482,853  
DATED : January 9, 1996  
INVENTOR(S) : Suzanne B. Sandmeyer It is certified that error appears in the above-indentified patent and that said Letters Patent is hereby corrected as shown below:

In column 12, line 22, please delete "I".

In column 12, line 26, please delete "monoctonal" and replace therefor with --monoclonal--.

In column 12, line 28, please delete "Milsrein" and replace therefor with --Milstein--.

In column 13, line 14, please delete "BioloGy" and replace therefor with --Biology--.

In column 13, line 14, please delete "(urz3-)" and replace therefor with --(ura3-)--.

In column 13, line 48, please delete "tRNA.gene" and replace therefor with --tRNA gene--.

In column 13, line 60, please center "EXAMPLE 4".

In column 14, line 36, please insert the underlined portion so the sequence is CAGTCTCATAACTGCGGATCCTTGTTT.

In column 14, line 38, please insert the underline to the portion so the sequence is CGTTCAGGATCCCGTATTGTCATACT.

In column 14, line 49, please insert the underline to the portion so the sequence is CAAAAGTAAAGGATCCAGGCATCA.

In column 14, line 51, please insert the underline to the portion so the sequence is ATGTCAGGGTCAGGGGATCCTA.

UNITED STATES PATENT AND TRADEMARK OFFICE
CERTIFICATE OF CORRECTION

PATENT NO. : 5,482,853
DATED : January 9, 1996
INVENTOR(S) : Suzanne B. Sandmeyer It is certified that error appears in the above-indentified patent and that said Letters Patent is hereby corrected as shown below:

In column 15, line 34, please delete "am" and replace therefor with --are--.

In column 16, line 8, please delete "hoeR-marked" and replace therefor with --neoR-marked--.

In column 16, line 18, please delete "when" and replace therefor with --then--.

In column 16, line 25, please delete "orobes" and replace therefor with --probes--.

In column 16, line 50, please delete "Milsrein" and replace therefor with --Milstein--.

In column 16, line 67, please delete "adjuvantsuspension" and replace therefor with --adjuvant suspension--.

In Claim 1, line 58 of column 23, please delete "nucleicacid" and replace therefor with --nucleic acid--.

In Claim 3, column 23, line 61, please delete "modified".

In Claim 10, column 25, line 2, please delete "the" (2nd occurrence) and replace therefor with --an--.

UNITED STATES PATENT AND TRADEMARK OFFICE
CERTIFICATE OF CORRECTION

PATENT NO. : 5,482,853
DATED : January 9, 1996
INVENTOR(S) : Suzanne B. Sandmeyer It is certified that error appears in the above-identified patent and that said Letters Patent is hereby corrected as shown below:

In Claim 12(a), column 25, line 29, please delete "position-Specific" and replace therefor with --position-specific--.

Signed and Sealed this

Twenty-ninth Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 1350 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GCAGTTATGA | GACTATATCA | TGACCATACC | TTATTTGGAG | GACATTTTGG | TGTAACAGTG | 60 |
| ACCCTTGCGA | AAATCAGCCC | AATTTACTAT | TGGCCAAAAT | TACAACATTG | CATCATACAA | 120 |
| TACATCAGGA | CCTGCGTACA | ATGTCAACTA | ATAAAATCAC | ACCGACCACG | CTTACATGGA | 180 |
| CTATTACAAC | CACTCCCTAT | AGCAGAAGGA | AGATGGCTTG | ATATATCAAT | GGATTTTGTG | 240 |
| ACAGGATTAC | CCCCGACATC | AAATAACTTG | AATATGATCC | TCGTCGTAGT | TGATCGTTTT | 300 |
| TCGAAACGCG | CTCACTTCAT | AGCTACAAGG | AAAACCTTAG | ACGCAACACA | ACTAATAGAT | 360 |
| CTACTCTTTC | GATACATTTT | TTCATATCAT | GGTTTTCCCA | GGACAATAAC | CAGTGATAGA | 420 |
| GATGTCCGTA | TGACCGCCGA | CAAATATCAA | GAACTCACGA | AAAGACTAGG | AATAAAATCG | 480 |
| ACAATGTCTT | CCGCGAACCA | CCCCCAAACA | GATGGACAAT | CCGAACGAAC | GATACAGACA | 540 |
| TTAAACAGGT | TACTAAGAGC | CTATGCTTCA | ACCAATATTC | AGAATTGGCA | TGTATATTTA | 600 |
| CCACAAATCG | AATTTGTTTA | CAATTCTACA | CCTACTAGAA | CACTTGGAAA | ATCACCATTT | 660 |
| GAAATTGATT | TAGGATATTT | ACCGAATACC | CCTGCTATTA | AGTCAGATGA | CGAAGTCAAC | 720 |
| GCAAGAAGTT | TTACTGCCGT | AGAACTTGCC | AAACACCTCA | AGCCCTTAC | CATCCAAACG | 780 |
| AAGGAACAGC | TAGAACACGC | TCAAATCGAA | ATGGAAACTA | ATAACAATCA | AAGACGTAAA | 840 |
| CCCTTATTGT | TAAACATAGG | AGATCACGTA | TTAGTGCATA | GAGATGCATA | CTTCAAGAAA | 900 |
| GGTGCTTATA | TGAAAGTACA | ACAAATATAC | GTCGGACCAT | TTCGAGTTGT | CAAGAAAATA | 960 |
| AACGATAACG | CCTACGAACT | AGATTTAAAC | TCTCACAAGA | AAAAGCACAG | AGTTATTAAT | 1020 |
| GTACAATTCC | TGAAAAAGTT | TGTATACCGT | CCAGACGCGT | ACCCAAAGAA | TAAACCAATC | 1080 |
| AGCTCCACTG | AAAGAATTAA | GAGAGCACAC | GAAGTTACTG | CACTCATAGG | AATAGATACT | 1140 |

| | | | | | |
|---|---|---|---|---|---|
| ACACACAAAA | CTTACTTATG | TCACATGCAA | GATGTAGACC | CAACACTTTC | AGTAGAATAC | 1200
| TCAGAAGCTG | AATTTTGCCA | AATTCCCGAA | AGAACACCAA | GATCAATATT | AGCCAACTTT | 1260
| AGACAACTCT | ACGAAACACA | AGACAACCCT | GAGAGAGAGG | AAGATGTTGT | ATCTCAAAAT | 1320
| GAGATATGTC | AGTATGACAA | TACGTCACCC | | | | 1350

( 2 ) INFORMATION FOR SEQ ID NO:2:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | |
|---|---|---|---|---|
| TGTTGTATCT | CAAAATGAGA | TATGTCAGTA | TGACAATACG | TCACCCTGAA | 50

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | |
|---|---|---|---|---|
| TATTAGGATT | GTCAAGACAC | TCCGGTATTA | CTCGAGCCCG | TAATACAACA | 50

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | |
|---|---|---|---|
| CAGTCTCATA | ACTGCGGATC | CTTGTTTTAT | TGG | 33

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | |
|---|---|---|
| CGTTCAGGAT | CCCGTATTGT | CATACTGAC | 29

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CAAAAGTAAA GGATCCAGGC ATCACAGG 28

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATGTCAGGGT CAGGGGATCC TACAAGGGGC GGGGG 35

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCCGGACGAG CCCCCGGGGA CGGGTAG 27

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCCAAAGCCT ACAGGGCCCC CCTTTTTCTG G 31

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CCGGTATTAC TCGACCCGTA ATACAACACC 30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CCGGGGTGTT GTATTACGGG TCGAGTAATA 30

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGCCTGTTGT ATCTCAAAAT GAGATATGT          29

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGCCACATAT CTCATTTTGA GATACAACA          29

(2) INFORMATION FOR SEQ ID NO:14:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:14:

UAUUAGGAUU GUCAAGACAC UCCGGUAUUA CUCGAGCCCG UAAUACAACA          50

(2) INFORMATION FOR SEQ ID NO:15:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:15:

UGUUGUAUCU CAAAAUGAGA UAUGUCAGUA UGACAAUACG UCACCCUGAA          50